United States Patent
Bang et al.

(10) Patent No.: US 10,913,679 B2
(45) Date of Patent: Feb. 9, 2021

(54) MISERITE CRYSTALLIZED GLASS FOR ARTIFICIAL TOOTH AND METHOD FOR COLORING SAME

(71) Applicant: SOONCHUNHYANG UNIVERSITY INDUSTRY ACADEMY COOPERATION FOUNDATION, Asan-si (KR)

(72) Inventors: Jae-Chul Bang, Seoul (KR); Young-Joo Song, Seoul (KR); Si-Won Sung, Incheon (KR); Seung-Bum Park, Cheonan-si (KR)

(73) Assignee: SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 0 days.

(21) Appl. No.: 16/330,303
(22) PCT Filed: Oct. 27, 2016
(86) PCT No.: PCT/KR2016/012190
§ 371 (c)(1),
(2) Date: Mar. 4, 2019
(87) PCT Pub. No.: WO2018/043803
PCT Pub. Date: Mar. 8, 2018

(65) Prior Publication Data
US 2019/0225533 A1 Jul. 25, 2019

(30) Foreign Application Priority Data

Sep. 2, 2016 (KR) .................. 10-2016-0113190

(51) Int. Cl.
*C03C 4/02* (2006.01)
*C03C 3/087* (2006.01)
(Continued)

(52) U.S. Cl.
CPC ............. *C03C 4/02* (2013.01); *A61C 13/08* (2013.01); *C03C 3/078* (2013.01); *C03C 3/087* (2013.01);
(Continued)

(58) Field of Classification Search
CPC ....... C03C 4/02; C03C 4/0028; C03C 4/0021; C03C 3/087; C03C 3/078; C03C 3/112; C03C 10/0009; A61C 13/08; A61K 6/836
See application file for complete search history.

(56) References Cited

U.S. PATENT DOCUMENTS 6,130,178 A 10/2000 Andrus et al.

FOREIGN PATENT DOCUMENTS

| JP | S58-91043 A | 5/1983 |
| JP | S63-176335 A | 7/1988 |

(Continued)

OTHER PUBLICATIONS

Hamedani et al. Effect of composition and heat treatment on the phase evolution andmechanical properties of tough miserite-based glass ceramics. Journal of Non-Crystalline Solids. vol. 382, Dec. 15, 2013, pp. 112-120.*

(Continued)

*Primary Examiner* — Noah S Wiese
(74) *Attorney, Agent, or Firm* — Hauptman Ham, LLP (57) ABSTRACT

Disclosed are a miserite crystallized glass for an artificial tooth and a method for coloring same, the method enabling a production of a uniform shade without degrading the physical properties of a crystallized glass by means of simply adding a small amount of coloring additive powder when preparing the crystallized glass. A miserite crystallized glass for an artificial tooth according to the present invention is colored with any one of the shades in groups A, B, C and D of the Vita shade guide which is a tooth shade reference. The miserite crystallized glass has a miserite crystal phase as the main phase and comprises a hydroxyapatite crystal phase and a xonotlite crystal phase as additional phases.

7 Claims, 5 Drawing Sheets

(51) Int. Cl.
*C03C 3/095* (2006.01)
*A61C 13/08* (2006.01)
*C03C 3/078* (2006.01)
*C03C 4/00* (2006.01)
*A61K 6/836* (2020.01)

(52) U.S. Cl.
CPC ............ *C03C 3/095* (2013.01); *C03C 4/0021* (2013.01); *C03C 4/0028* (2013.01); *A61K 6/836* (2020.01); *C03C 2201/3423* (2013.01); *C03C 2201/3476* (2013.01); *C03C 2203/10* (2013.01)

(56) References Cited

FOREIGN PATENT DOCUMENTS

| KR | 10-2012-0073710 A | 7/2012 |
| KR | 10-2014-0063526 A | 5/2014 |
| KR | 10-1556899 B1 | 10/2015 |
| KR | 10-2016-0027357 A | 3/2016 |
| KR | 10-1616947 B1 | 5/2016 |

OTHER PUBLICATIONS

Salman et al. The crystallization behaviour and bioactivity of wollastoniteglass-ceramic based on Na2O—K2O—CaO—SiO2—F glass system. Journal of Asian Ceramic Societies 3 (2015) 255-261.*

M.T. Hamedani et al., Effect of composition and heat treatment on the phase evolution and mechanical properties of tough miserite-based glass ceramics, Journal of Non-Crystalline Solids, 2013, pp. 112-120, vol. 382, Elsevier B.V.

Jae Chul Bang, Synthesis of Miserite or Wollastonite Glass-ceramics for Dental Applications, 2nd International Conference and Expo on Ceramics & Composite Materials, Jul. 25-26, 2016, Conference Series LLC, Berlin, Germany.

International Search Report for PCT/KR2016/012190 dated May 22, 2017.

Office Action issued for corresponding Japanese Patent Application No. 2019-534612 dated Jun. 9, 2020.

* cited by examiner

MISERITE CRYSTALLIZED GLASS FOR ARTIFICIAL TOOTH AND METHOD FOR COLORING SAME

TECHNICAL FIELD

The present disclosure relates to a miserite-based crystallized glass for an artificial tooth and a method for coloring the same. More particularly, the present disclosure relates to a miserite-based crystallized glass for an artificial tooth and a method for coloring the same, in which in a production of the crystallized glass, addition of a small amount of coloring additive powders allows a uniform shade to be rendered without degrading properties of the glass.

BACKGROUND

Since natural tooth shades vary considerably depending on races or ages, it is very important to accurately adapt artificial tooth shades to the natural tooth shades of patients. At present, stabilized zirconia widely used as the artificial tooth has a low light transmittance and thus is poorly aesthetic. Further, the stabilized zirconia has its own shade, which makes it difficult to adapt the shade thereof to the natural tooth shade.

For this reason, lithium disilicate crystallized glass has been recently used because the lithium disilicate crystallized glass has a suitable visible light transmittance and thus is superior in aesthetics, and has excellent mechanical properties. However, because the lithium disilicate crystallized glass has an inherent shade, it may be difficult to render and control the shade thereof.

Recently, efforts have been made to study a novel crystallized glass for an artificial tooth in a current situation where the crystallized glass for the artificial tooth is substantially limited to the lithium disilicate based crystallized glass.

As Related Prior art, Korean Patent Application Publication No. 10-2014-0063526 (published on May 27, 2014) describes a doping or coloring method of ceramics, glass ceramics, or glasses.

In the Prior Art as described above, a solution containing a coloring element is produced (by dissolving a corresponding metal salt into a corresponding solvent), and then is sprayed. However, in this approach, there is a disadvantage that a production step is further added, and a shade is likely to be rendered unevenly.

DISCLOSURE

Technical Purposes

A purpose of the present disclosure is to provide a miserite-based crystallized glass for an artificial tooth and a method for coloring the same in which the glass meets mechanical properties needed to be used as the artificial tooth, and when the glass has been crystallized, the glass renders a bright white, thereby to allow shade render and control of the artificial tooth to be easy.

Technical Solutions

In one aspect of the present disclosure, there is provided a method for coloring a miserite-based crystallized glass for an artificial tooth, the method comprising: (a) drying, weighing and ball-milling raw glass powders and coloring additive powders, wherein the raw glass powders includes $SiO_2$, CaO, $CaF_2$ and $K_2O$; (b) introducing the ball-milled raw glass powders and coloring additive powders into a furnace, and calcining the powders therein at 950 to 1050° C. for 1 to 3 hours, and then cooling the powders to a room temperature; (c) melting the calcined powders to form a glass; (d) introducing the glass into a preheated mold at 450 to 550° C., preforming a thermal-stress removal heat-treatment of the glass at 450 to 550° C. for 1 to 3 hours, and cooling the glass to a room temperature; and (e) heat-treating the glass to crystalline the glass, and cooling the glass to a room temperature to form a crystallized glass.

In another aspect of the present disclosure, there is provided a miserite-based crystallized glass for an artificial, wherein the miserite-based crystallized glass is colored to have a shade of one of groups A, B, C, or D of a Vita shade guide as a tooth shade reference, wherein the miserite-based crystallized glass has a miserite crystal phase as a main phase and has a hydroxyapatite crystal phase and a xonotlite crystal phase as additional phases.

Technical Effects

In accordance with the miserite-based crystallized glass for the artificial tooth and the method for coloring the same according to the present disclosure, in the production of the crystallized glass for the artificial tooth, the coloring may be achieved by simply adding a small amount of the coloring additive powders to the raw glass powders, thereby rendering a uniform shade of the crystallized glass without degrading its inherent properties. Thus, the miserite-based crystallized glass may be used to perform coping and crowning of the artificial tooth.

As a result, the miserite-based crystallized glass for the artificial tooth as produced by the method in accordance with the present disclosure may be colored to have a shade of one of groups A, B, C, or D of the Vita shade guide as a tooth shade reference. The miserite crystallized glass has a miserite crystal phase as a main phase and has a hydroxyapatite crystal phase and a xonotlite crystal phase as additional phases.

Further, the miserite-based crystallized glass for the artificial tooth as produced by the method in accordance with the present disclosure may exhibit a Vickers hardness 6.5 to 7.2 GPa, a fracture toughness 2.5 to 3.2 MPa·m$^{-2}$, a flexural strength 300 to 360 MPa and a 1 mm thickness-based visible-light transmittance 30 to 40%.

DETAILED DESCRIPTIONS

Advantages and features of the present disclosure, and methods to accomplish the advantages and features will become apparent with reference to embodiments, which is described in detail below with reference to the accompanying drawings. However, the present disclosure may not be limited to the embodiments as described below, but may be embodied in various different forms. The embodiments only makes the present disclosure complete and may be provided to fully set forth the scope of the present disclosure to those skilled in the art. The present disclosure is only defined by the scope of the claims. Like reference numerals refer to like elements herein.

Hereinafter, a miserite-based crystallized glass for an artificial tooth and a method for coloring the same according to preferred embodiments of the present disclosure will be described in detail with reference to the accompanying drawings.

Figure 1:
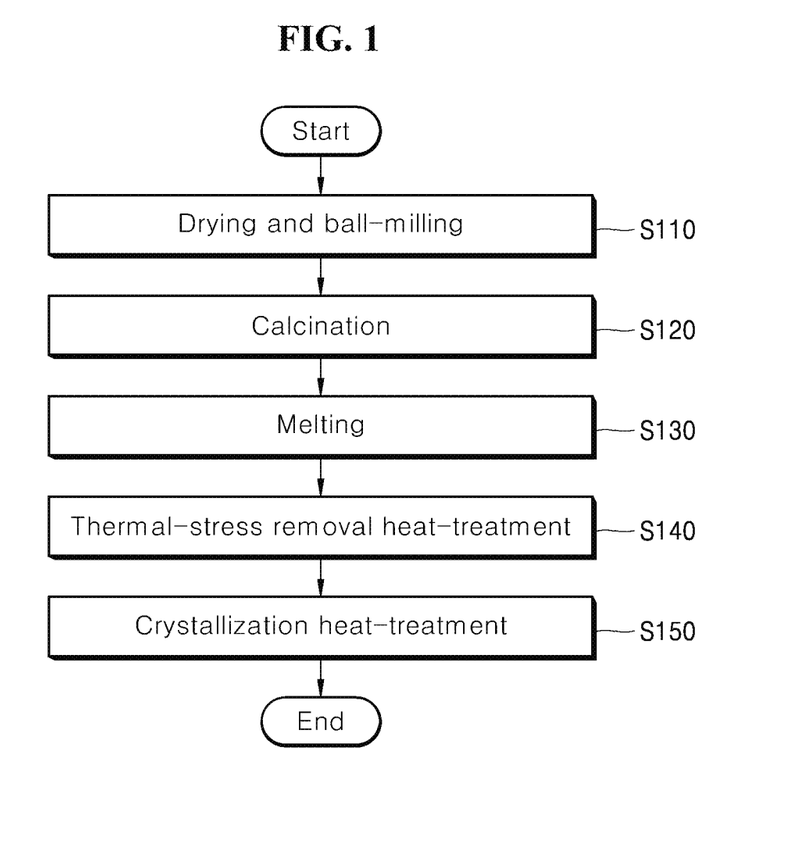
FIG. 1 is a process flow diagram showing a coloring method of a miserite-based crystallized glass for an artificial tooth according to an embodiment of the present disclosure.

FIG. 1 is a process flow diagram showing a method for coloring a miserite-based crystallized glass for an artificial tooth according to an embodiment of the present disclosure.

Referring to FIG. 1, a method for coloring a miserite-based crystallized glass for an artificial tooth according to an embodiment of the present disclosure may include a drying and ball-milling step S110, a calcination step S120, a melting step S130, a thermal-stress removal heat-treatment step S140, and a crystallization heat-treatment step S150.

Drying and Ball-Milling

The drying and ball-milling step S110 may dry raw glass powders including $SiO_2$, $CaO$, $CaF_2$ and $K_2O$, and coloring additive powders, weigh the dried powders and ball-mill the dried powders.

In this connection, the drying may be carried out to remove moisture from the raw glass powders and coloring additive powders. The drying is preferably carried out at 100 to 150 degrees C. for 30 to 120 minutes.

These raw glass powders may be composed of mixed powders including $SiO_2$, $CaO$, $CaF_2$ and $K_2O$ in order to produce the crystallized glass having a miserite crystal phase having a chemical composition $[KCa_5(Si_2O_7)(Si_6O_{15})(OH)F]$ as a main phase.

More specifically, the raw glass powders preferably have a composition of 50 to 55% by weight of $SiO_2$, 24 to 30% by weight of $CaO$, 10 to 15% by weight of $CaF_2$ and 5 to 10% by weight of $K_2O$.

$SiO_2$ serves to form a glass network structure and is a main component of the miserite crystal phase. It is preferable that such $SiO_2$ is added at a content of 50 to 55% by weight based on the total weight of the raw glass powders. When the addition amount of $SiO_2$ is smaller than 50% by weight, the miserite crystal phase may not be formed and excessive crystallization may lower the light transmittance of the glass. On the contrary, when the addition amount of $SiO_2$ exceeds 55% by weight, the crystallization does not proceed well, and, especially, the miserite crystal phase may not be formed, and strength and toughness of the resulting glass may be insufficient.

$CaO$ is a main component of the miserite crystal phase and is preferably added in a content of 24 to 30% by weight based on the total weight of the raw glass powders. When the amount of $CaO$ as added is smaller than 24 wt %, the miserite crystal phase may not be formed. On the other hand, when the amount of $CaO$ added exceeds 30% by weight, the strength of the glass may be insufficient.

$CaF_2$ is a main component of the miserite crystal phase and is added for exhibiting a effect of preventing dental caries and inhibiting microbial propagation. It is preferable that such $CaF_2$ is added at a content of 10 to 15% by weight based on the total weight of the raw glass powders. When the added amount of $CaF_2$ is smaller than 10% by weight, the miserite crystal phase may be hardly formed, and dental caries prevention and microbial growth inhibition may not be realized. On the contrary, when the amount of $CaF_2$ added exceeds 15% by weight, this raises the production cost, which is not economical.

$K_2O$ improves a melting ability during melting for glass formation and plays a role in promoting the formation of the miserite crystal phase. $K_2O$ is preferably added in a content of 5 to 10% by weight based on the total weight of the raw glass powders. When the amount of $K_2O$ added is smaller than 5% by weight, the addition amount is insignificant, thus, to make it difficult to form the miserite crystal phase. On the other hand, when the amount of $K_2O$ added exceeds 10% by weight, the strength of the glass may be lowered.

Figure 2:
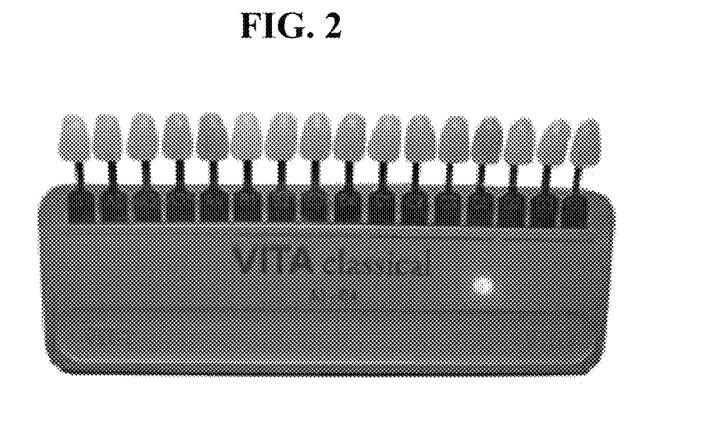
FIG. 2 shows the Vita shade guide as a tooth shade reference.

FIG. 2 shows the Vita shade guide as a tooth shade reference.

Referring to FIG. 2, coloring additive powders are preferably added such that the resulting glass is colored to have one of the shades in groups A, B, C and D of the Vita shade guide as a tooth shade reference while not degrading the properties of the glass.

In a comparison example, the miserite-based crystallized glass for the artificial tooth may be produced by crystallization heat-treatment of only the raw glass powders without the coloring additives. In this case, the crystallized glass renders a bright white color. To the contrary, in accordance with the present disclosure, the coloring may be achieved by simply adding a small amount of the coloring additive powders to the raw glass powders. In this case, the crystallized glass for the artificial tooth may exhibit uniform shade rendering and thus excellent aesthetics without deteriorating the inherent physical properties thereof.

Thus, in the method for coloring the miserite-based crystallized glass for an artificial tooth according to an embodiment of the present disclosure, the coloring is performed by directly mixing the coloring additive powders with the raw glass powders and then by melting the mixture. Thus, not only a separate process such as a spray coating may be omitted, but also a uniform shade may be rendered.

Such coloring additive powders may include an oxide of at least one selected from a group consisting of Er, Fe, Cr, Mn, V, Cu, and Ce. More concretely, the oxide may include at least one selected from a group consisting of $Er_2O_3$, $Fe_2O_3$, $Cr_2O_3$, $Mn_2O_3$, $V_2O_5$, $CuO$ and $CeO_2$.

In this connection, the coloring additive powders are preferably added in an amount of 0.001 to 5 parts by weight based on 100 parts by weight of the raw glass powders. When the amount of the coloring additive powders as added is smaller than 0.001 part by weight based on 100 parts by weight of the raw glass powders, the addition amount thereof is insufficient, thereby to make it difficult to exhibit the coloring effect properly. On the contrary, when the addition amount of the coloring additive powders exceeds 5 parts by weight with respect to 100 parts by weight of the raw glass powders, this may raise the production cost without increasing the coloring effect, and may cause a problem of deteriorating the mechanical properties of the crystallized glass.

Calcination

In the calcination step S120, ball-milled raw glass powders and coloring additive powders are put into a furnace, then calcined at 950 to 1050° C. for 1 to 3 hours, and then cooled to a room temperature.

When the mixture powders are calcined at 950 to 1050° C. for 1 to 3 hours, organic components as an impurity may be burned and discharged to the outside, and carbon dioxide gas may be generated and discharged to the outside.

When the calcination temperature is lower than 950° C. or the calcination duration is smaller than 1 hour, the organic component and carbon dioxide are not completely removed and remain. Thus, during subsequent crystallization heat-treatment, the properties of the crystallized glass may be degraded. Conversely, when the calcination temperature exceeds 1050° C. or the calcination duration exceeds 3 hours, this may be a factor that lowers a production yield without further increase in the effect. This is not preferable.

In this connection, the cooling is preferably performed in a cooling-in-furnace manner. When air-cooling or water-cooling is applied, internal stress is severely formed in the glass. In some cases, cracking may occur. Thus, cooling the glass in the furnace is preferable. In this connection, the room temperature may be in a range of 1 to 40° C., but may not be limited thereto.

Melting

In the melting step S130, the calcined powders are melted to form the glass.

In this connection, in the melting step, it is preferable to add the calcined powders to a melting furnace, raise a temperature to 1300 to 1400° C. at a rate of 8 to 12° C./min, and then perform melting at 1300 to 1400° C. for 10 to 60 minutes.

When the temperature rise rate is lower than 8° C./min, the productivity is low because the duration is long. On the other hand, when the temperature rise rate exceeds 12 degrees C./min, the volatilized amount of the raw glass powders and the coloring additive powders is increased, which may act as a factor for lowering the physical properties of the crystallized glass.

In this connection, when the melting temperature is lower than 1300° C. or when the melting duration is smaller than 10 minutes, the raw glass powders and coloring additive powders are not completely melted and a moldability is deteriorated. Conversely, when the melting temperature exceeds 1400° C. or the melting duration exceeds 60 minutes, excessive energy and duration are required, which is not economical.

Thermal-Stress Removal Heat-Treatment

In the thermal-stress removal heat-treatment step S140, the glass is poured into a mold preheated to 450 to 550° C., followed by thermal-stress removal heat treatment at 450 to 550° C. for 1 to 3 hours and then cooled to a room temperature.

In this connection, when the thermal-stress removal heat-treatment temperature is lower than 450° C., or when the thermal-stress removal heat-treatment duration is smaller than 1 hour, it may be difficult to completely remove the thermal stress from the glass. Conversely, when the thermal-stress removal heat-treatment temperature exceeds 550° C. or the thermal-stress removal heat-treatment duration exceeds 3 hours, this may not be economical because this takes excessive energy and duration and further may lead to the formation of unwanted crystal phases.

Crystallization Heat-Treatment

In the crystallization heat-treatment step S150, the glass is heat-treated and crystallized and then cooled to a room temperature to form the crystallized glass.

In this connection, the crystallization heat-treatment step may be subdivided into following 3 sub-steps: a nucleation heat-treatment sub-step of heat-treating the glass at 580 to 630° C. for 30 minutes to 120 minutes; a first crystallization heat-treatment sub-step that heat-treats the glass at 780 to 860° C. for 3 to 7 hours; and a second crystallization heat-treatment sub-step of heat treatment of the glass at 1000 to 1080° C. for 3 to 7 hours.

Thus, the three-stage heat treatment consisting of the nucleation heat-treatment sub-step, first crystallization heat-treatment sub-step and second crystallization heat-treatment sub-step may allow the crystallized glass to be produced more stably than in a single stage heat treatment.

In this connection, when the second crystallization heat-treatment temperature is lower than 1000° C. or the second crystallization heat-treatment duration is smaller than 3 hours, crystallization may be insufficient due to the incomplete heat-treatment. Conversely, when the second crystallization heat-treatment temperature exceeds 1080° C., or when the second crystallization heat-treatment duration exceeds 7 hours, this may cause a problem of deterioration of mechanical properties due to grain growth due to the excessive heat treatment.

In accordance with the method for coloring the miserite-based crystallized glass for the artificial tooth according to the present disclosure, in the production of the crystallized glass for the artificial tooth, the coloring may be achieved by simply adding a small amount of the coloring additive powders to the raw glass powders, thereby rendering a uniform shade of the crystallized glass without degrading its inherent properties. Thus, the miserite-based crystallized glass may be used to perform coping and crowning of the artificial tooth.

As a result, the miserite-based crystallized glass for the artificial tooth as produced by the method in accordance with the present disclosure may be colored to have a shade of one of groups A, B, C, or D of the Vita shade guide as a tooth shade reference. The miserite crystallized glass has a miserite crystal phase as a main phase and has a hydroxyapatite crystal phase and a xonotlite crystal phase as additional phases.

Further, the miserite-based crystallized glass for the artificial tooth as produced by the method in accordance with the present disclosure may exhibit a Vickers hardness 6.5 to 7.2 GPa, a fracture toughness 2.5 to 3.2 MPa·m$^{-2}$, a flexural strength 300 to 360 MPa and a 1 mm thickness-based visible-light transmittance 30 to 40%.

Present Example

Hereinafter, a preferred Present Example is illustrated to help understand the present disclosure. It will be apparent to those skilled in the art that various modifications and variations are possible within the scope and spirit of the present disclosure, and such variations and modifications fall within the scope of the appended claims.

Specimen Production

As specimens, colored crystallized glasses for the artificial tooth according to Present Examples 1 to 26 were produced with compositions and process conditions as indicated in Table 1.

In this connection, according to Present Examples 1 to 26, after the addition of the raw glass powders and coloring additive powders to a drying machine for moisture removal, the mixture was dried at 120° C. for 1 hour therein.

Then, the dried raw glass powders and coloring additive powders were weighed according to the compositions shown in Table 1, and subjected to the dry ball-milling for 24 hours.

Then, the ball-milled raw glass powders and coloring additive powders were sieved and placed in a platinum crucible.

Next, the platinum crucible was charged into an electric furnace for calcination. A temperature of the electric furnace was raised to 1000° C. at a temperature rise rate of 10° C./min. Thereafter, the furnace was maintained at 1000° C. for 1 hour and 30 minutes. Then, the cooling-in-furnace was executed at the room temperature 15 degrees C. to form a glass.

Subsequently, the calcined glass was put into a melting furnace, which was heated to 1360° C. at a temperature rise rate of 10° C./min, and then maintained at 1360° C. for 30 minutes for melting of the glass.

Next, the molten glass was poured into a preheated graphite mold at 500° C. The graphite mold was maintained at 500° C. for 2 hours to perform the thermal-stress removal heat-treatment, and then cooled to the room temperature.

After the crystallization heat treatment of the glass, the colored crystallized glass specimen for the artificial tooth was produced via the cooling-in-furnace to the room temperature.

In this crystallization heat-treatment, for the specimens according to Present Examples 1 to 13, 3 stages heat-treatment was performed as follows: first, for 1 hour and at the nucleation temperature of 610° C.; second, for 5 hours and at first crystallization temperature of 800° C.; and, third, at the second heat-treatment temperature of 1010° C. and for 5 hours.

Further, in this crystallization heat-treatment, for the specimens according to Present Examples 14 to 26, 3 stages heat-treatment was performed as follows: first, for 1 hour and at the nucleation temperature of 610° C.; second, for 5 hours and at first crystallization temperature of 800° C.; and, third, at the second heat-treatment temperature of 1060° C. and for 5 hours.

TABLE 1

| Examples | Raw glass powders (wt %) | Coloring additive powders Type | Content (wt %) | Nucleation temperature | crystallization heat-treatment temperature (° C.) First crystallization temperature | Second crystallization temperature |
|---|---|---|---|---|---|---|
| Present Example 1 | $SiO_2$—CaO—$CaF_2$—$K_2O$ (53.01-26.29-12.91-7.79) | $Er_2O_3$ | 0.1 | 610 | 800 | 1010 |
| Present Example 2 | | $Er_2O_3$ | 0.5 | | | |
| Present Example 3 | | $Er_2O_3$ | 0.8 | | | |
| Present Example 4 | | $Fe_2O_3$ | 0.1 | | | |
| Present Example 5 | | $Fe_2O_3$ | 0.3 | | | |
| Present Example 6 | | $Fe_2O_3$ | 0.5 | | | |
| Present Example 7 | | $CeO_2$ | 2 | | | |
| Present Example 8 | | $CeO_2$ | 3 | | | |
| Present Example 9 | | $Cr_2O_3$ | 0.01 | | | |
| Present Example 10 | | $Cr_2O_3$ | 0.02 | | | |
| Present Example 11 | | $V_2O_5$ | 0.1 | | | |
| Present Example 12 | | $V_2O_5$ | 0.3 | | | |
| Present Example 13 | | $V_2O_5$ | 0.5 | | | |
| Present Example 14 | $SiO_2$—CaO—$CaF_2$—$K_2O$ (53.01-26.29-12.91-7.79) | $Er_2O_3$ | 0.1 | 610 | 850 | 1060 |
| Present Example 15 | | $Er_2O_3$ | 0.5 | | | |
| Present Example 16 | | $Er_2O_3$ | 0.8 | | | |
| Present Example 17 | | $Fe_2O_3$ | 0.1 | | | |
| Present Example 18 | | $Fe_2O_3$ | 0.3 | | | |
| Present Example 19 | | $Fe_2O_3$ | 0.5 | | | |
| Present Example 20 | | $CeO_2$ | 2 | | | |
| Present Example 21 | | $CeO_2$ | 3 | | | |
| Present Example 22 | | $Cr_2O_3$ | 0.01 | | | |
| Present Example 23 | | $Cr_2O_3$ | 0.02 | | | |
| Present Example 24 | | $V_2O_5$ | 0.1 | | | |
| Present Example 25 | | $V_2O_5$ | 0.3 | | | |
| Present Example 26 | | $V_2O_5$ | 0.5 | | | |

2. Property Evaluation

Table 2 shows mechanical and optical properties of the colored crystallized glass specimens for the artificial tooth according to Present Examples 1 to 26.

TABLE 2

| Examples | Vickers hardness (GPa) | Fracture toughness (MPa · m$^{-2}$) | flexural strength (MPa) | Visible-light transmittance (%, 1 mm thick specimen) |
|---|---|---|---|---|
| Present Example 1 | 6.7 | 2.8 | 321 | 37 |
| Present Example 2 | 6.7 | 2.9 | 324 | 36 |
| Present Example 3 | 6.8 | 2.7 | 320 | 37 |
| Present Example 4 | 6.7 | 2.8 | 319 | 37 |
| Present Example 5 | 6.8 | 2.9 | 322 | 36 |
| Present Example 6 | 6.9 | 2.7 | 321 | 36 |
| Present Example 7 | 6.7 | 2.8 | 320 | 37 |
| Present Example 8 | 6.8 | 2.7 | 322 | 35 |
| Present Example 9 | 6.8 | 2.8 | 321 | 37 |
| Present Example 10 | 6.7 | 2.9 | 322 | 36 |
| Present Example 11 | 6.8 | 2.8 | 321 | 37 |
| Present Example 12 | 6.7 | 2.7 | 320 | 37 |
| Present Example 13 | 6.8 | 2.8 | 319 | 36 |
| Present Example 14 | 7.0 | 2.9 | 326 | 33 |
| Present Example 15 | 7.1 | 2.9 | 327 | 32 |
| Present Example 16 | 7.0 | 3.0 | 325 | 35 |
| Present Example 17 | 7.1 | 2.8 | 326 | 34 |
| Present Example 18 | 6.9 | 2.9 | 327 | 33 |
| Present Example 19 | 7.0 | 3.0 | 328 | 34 |
| Present Example 20 | 7.0 | 3.0 | 326 | 32 |
| Present Example 21 | 7.1 | 2.9 | 325 | 33 |
| Present Example 22 | 7.0 | 3.0 | 324 | 34 |
| Present Example 23 | 6.9 | 3.0 | 326 | 34 |
| Present Example 24 | 7.0 | 2.8 | 327 | 35 |
| Present Example 25 | 7.1 | 2.9 | 325 | 32 |
| Present Example 26 | 7.0 | 3.0 | 324 | 33 |

Referring to Table 1 and Table 2, it may be confirmed that for the specimens according to Present Examples 1 to 26, target values of the properties may be satisfied as follows: a Vickers hardness 6.5 to 7.2 GPa, a fracture toughness 2.5 to 3.2 MPa·m$^{-2}$, a flexural strength 300 to 360 MPa and a 1 mm thickness-based visible-light transmittance 30 to 40%.

Figure 3:
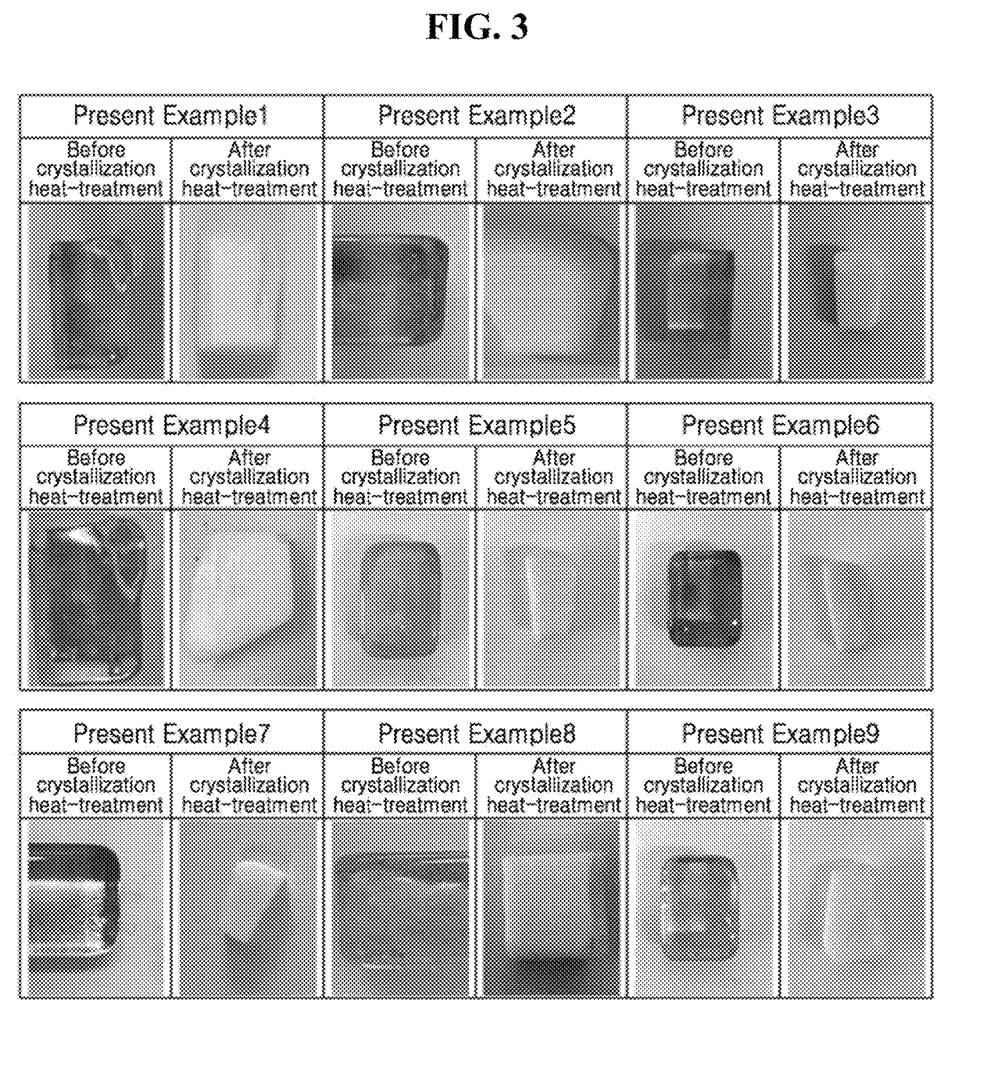
FIG. 3 shows a specimen before and after a crystallization heat-treatment according to Present Examples 1 to 9.
Figure 4:
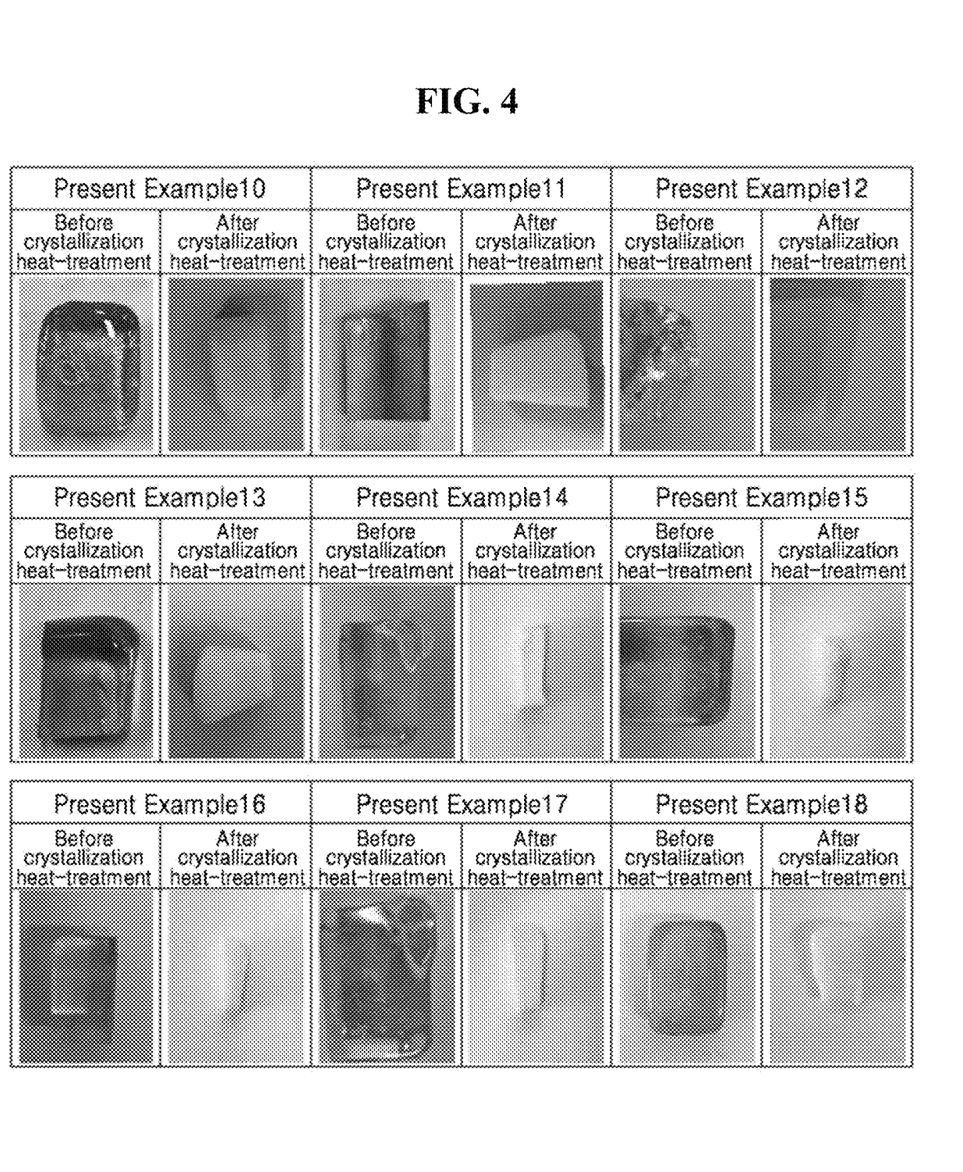
FIG. 4 shows a specimen before and after a crystallization heat treatment according to Present Examples 10 to 18.
Figure 5:
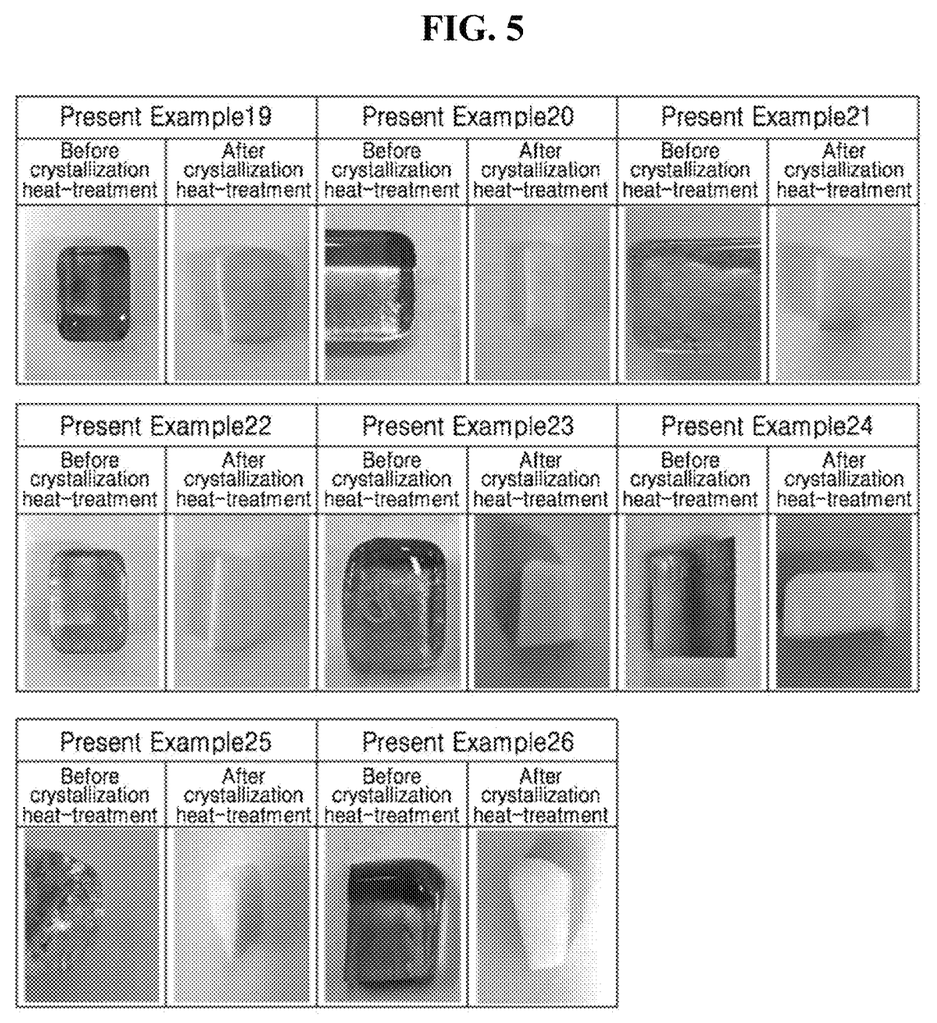
FIG. 5 shows a specimen before and after a crystallization heat treatment according to Present Examples 19 to 26.

FIG. 3 shows a specimen before and after a crystallization heat-treatment according to Present Examples 1 to 9. FIG. 4 shows a specimen before and after a crystallization heat treatment according to Present Examples 10 to 18. FIG. 5 shows a specimen before and after a crystallization heat treatment according to Present Examples 19 to 26.

As shown in FIG. 3 to FIG. 5, it may be confirmed that, in the specimens according to Present Examples 1 to 26, various shades are rendered depending on the types and contents of the coloring additive powders.

Therefore, it may be confirmed that when a small amount of the coloring additive powders is directly added so as to render the shades of groups A, B, C, and D in the Vita shade guide as a tooth shade reference, the uniform shade rendering of the glass may be realized without sacrificing the inherent properties of the crystallized glass for the artificial tooth.

In this connection, we may see that, in comparison between Present Examples 1 to 13 and Present Examples 14 to 26, the slight shade difference may occur therebetween. This may be attributed to a difference in the crystallization heat-treatment conditions, that is, the first and second crystallization heat-treatment temperatures.

Figure 6:
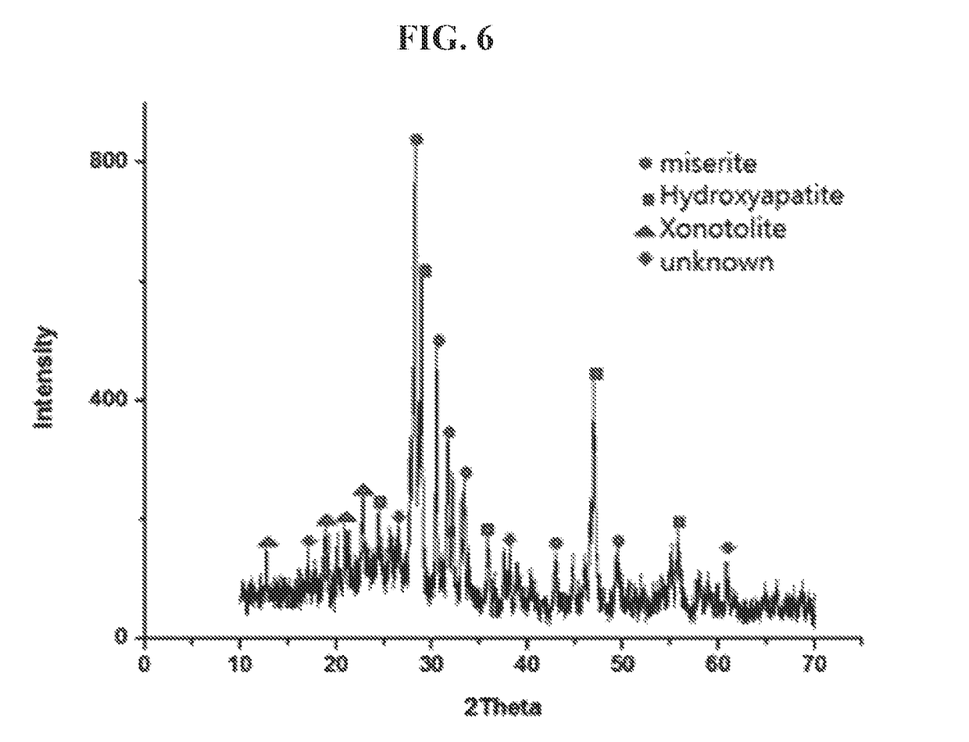
FIG. 6 is a graph showing XRD measurement results of a specimen according to Present Example 1.

FIG. 6 is a graph showing XRD measurement results of a specimen according to Present Example 1.

As shown in FIG. 6, in the specimen according to Present Example 1, a large number of miserite crystal peaks were observed in the X-ray diffraction phase analysis. Further, some hydroxyapatite crystal peaks and xonotolite crystal peaks were observed in the X-ray diffraction phase analysis.

Although the present disclosure has been described with reference to the embodiments of the present disclosure, various changes or modifications may be made in a level of the technician having ordinary knowledge in the technical field to which the present disclosure belongs. These changes and modifications may fall within the scope of the present disclosure unless they depart from the scope of the technical idea provided by the present disclosure. Accordingly, the scope of the present disclosure should be determined by the claims set forth below.

What is claimed is:

1. A method for coloring a miserite-based crystallized glass for an artificial tooth, the method comprising:
   (a) drying, weighing and ball-milling raw glass powders and coloring additive powders, wherein the raw glass powders includes $SiO_2$, CaO, $CaF_2$ and $K_2O$;
   (b) introducing the ball-milled raw glass powders and coloring additive powders into a furnace, and calcining the powders therein at 950 to 1050° C. for 1 to 3 hours, and then cooling the powders to a room temperature;
   (c) melting the calcined powders to form a glass;
   (d) introducing the glass into a preheated mold at 450 to 550° C., preforming a thermal-stress removal heat-treatment of the glass at 450 to 550° C. for 1 to 3 hours, and cooling the glass to a room temperature; and
   (e) heat-treating the glass to crystalline the glass, and cooling the glass to a room temperature to form a crystallized glass,
   wherein in (c), the melting includes increasing the calcined powders to 1300 to 1400° C. at an increase rate of 8 to 12° C./min, and then performing melting of the powders at 1300 to 1400° C. for 10 to 60 minutes.

2. The method of claim 1, wherein in (a), the weighing includes weighing the raw glass powders to have a composition of 50 to 55% by weight of $SiO_2$, 24 to 30% by weight of CaO, 10 to 15% by weight of $CaF_2$ and 5 to 10% by weight of $K_2O$.

3. The method of claim 1, wherein in (a), the coloring additive powders includes at least one selected from a group consisting of $Er_2O_3$, $Fe_2O_3$, $Cr_2O_3$, $Mn_2O_3$, $V_2O_5$, CuO and $CeO_2$.

4. The method of claim 1, wherein in (a), the coloring additive powders are added in a content of 0.001 to 5 parts by weight based on 100 parts by weight of the raw glass powders.

5. The method of claim 1, wherein in (e), the heat-treating includes:
- a nucleation heat-treatment in which the glass is heat-treated at 580 to 630° C. for 30 minutes to 120 minutes;
- a first crystallization heat-treatment in which the glass is heat-treated at 780 to 860° C. for 3 to 7 hours; and
- a second crystallization heat-treatment in which the glass is heat-treated at 1000 to 1080° C. for 3 to 7 hours.

6. A miserite-based crystallized glass for an artificial tooth produced by a method comprising:
- (a) drying, weighing and ball-milling raw glass powders and coloring additive powders, wherein the raw glass powders includes $SiO_2$, $CaO$, $CaF_2$ and $K_2O$;
- (b) introducing the ball-milled raw glass powders and coloring additive powders into a furnace, and calcining the powders therein at 950 to 1050° C. for 1 to 3 hours, and then cooling the powders to a room temperature;
- (c) melting the calcined powders to form a glass;
- (d) introducing the glass into a preheated mold at 450 to 550° C., preforming a thermal-stress removal heat-treatment of the glass at 450 to 550° C. for 1 to 3 hours, and cooling the glass to a room temperature; and
- (e) heat-treating the glass to crystalline the glass, and cooling the glass to a room temperature to form a crystallized glass, wherein the miserite-based crystallized glass is colored to have a shade of one of groups A, B, C, or D of a Vita shade guide as a tooth shade reference, and wherein the miserite-based crystallized glass has a miserite crystal phase as a main phase and has a hydroxyapatite crystal phase and a xonotlite crystal phase as additional phases.

7. The miserite-based crystallized glass of claim 6, wherein the miserite-based crystallized glass exhibits a Vickers hardness 6.5 to 7.2 GPa, a fracture toughness 2.5 to 3.2 MPa·m$^{-2}$, a flexural strength 300 to 360 MPa and a 1 mm thickness-based visible-light transmittance 30 to 40%.

* * * * *